(12) United States Patent
Holmes

(10) Patent No.: US 7,148,498 B1
(45) Date of Patent: Dec. 12, 2006

(54) EXTERNALLY CONTROLLED ELECTROMAGNETIC ENERGY SPOT CURING SYSTEM

(75) Inventor: Mark Holmes, Waterford, CT (US)

(73) Assignee: Henkel Corporation, Rocky Hill, CT (US)

( * ) Notice: Subject to any disclaimer, the term of this patent is extended or adjusted under 35 U.S.C. 154(b) by 0 days.

(21) Appl. No.: 10/875,586

(22) Filed: Jun. 25, 2004

(51) Int. Cl.
*A61N 5/00* (2006.01)
*G21G 5/00* (2006.01)

(52) U.S. Cl. ............ 250/504 R; 250/306; 250/307; 250/505.1; 34/245; 34/277

(58) Field of Classification Search ............ 250/504 R, 250/505.1, 492.1, 455.11, 454.11; 34/259, 34/255, 266, 275, 308, 277, 245
See application file for complete search history.

(56) References Cited

U.S. PATENT DOCUMENTS

| | | | |
|---|---|---|---|
| 4,574,138 A * | 3/1986 | Moran et al. ............... 524/786 |
| 5,521,392 A * | 5/1996 | Kennedy et al. .......... 250/492.1 |
| 5,803,729 A * | 9/1998 | Tsimerman .................. 433/29 |
| 5,843,143 A * | 12/1998 | Whitehurst ................... 607/88 |
| 6,520,663 B1 * | 2/2003 | Holmes et al. ............. 362/285 |
| 6,538,258 B1 * | 3/2003 | Rau et al. ............... 250/504 R |
| 6,835,679 B1 * | 12/2004 | Bilanin et al. ........... 250/493.1 |
| 6,874,249 B1 * | 4/2005 | Holmes ....................... 34/275 |
| 6,881,964 B1 * | 4/2005 | Holmes ................... 250/492.1 |
| 2004/0094727 A1 * | 5/2004 | Holmes .................. 250/504 R |
| 2005/0002599 A1 * | 1/2005 | Bohne et al. ................. 385/16 |

* cited by examiner

*Primary Examiner*—Nikita Wells
*Assistant Examiner*—Bernard Souw
(74) *Attorney, Agent, or Firm*—Steven C. Bauman

(57) ABSTRACT

The present invention provides an electromagnetic energy spot curing system which utilizes an external signal from a processor to control the operation of the curing unit. The processor is external to the curing unit and specifically controls the exposure and dwell periods of the radiation energy from the curing unit on a work site or target which contains material to be light cured.

17 Claims, 2 Drawing Sheets

EXTERNALLY CONTROLLED ELECTROMAGNETIC ENERGY SPOT CURING SYSTEM

FIELD OF THE INVENTION

The present invention relates generally to an electromagnetic energy spot curing system, and more particularly to a system that utilizes an external output signal from an external processor to control the operation of the UV curing unit.

BACKGROUND OF THE INVENTION

It is well known to use ultraviolet (UV) lamps to cure certain curable compounds such as adhesives and the like. UV spot curing systems are used in various applications including the curing of industrial sealants for potting electronics, bonding plastics in the medical industry and the curing of dental filling materials, disk industry amongst other applications.

Commercially available UV spot curing assemblies typically include a UV light or visible source, a reflector by which reflected light from the light source is focused on a target location of an object. Currently, spot curing systems use an internal timing device to control the exposure time of the light on the object.

One known light curing system is disclosed in U.S. Pat. No. 5,803,729. The light cure system described therein includes a light source, a light guide for delivering the light produced by the source to a work site, a dimmer for controlling the intensity of light delivered to the work site, and a shutter for controlling the exposure time for the work site. The system also includes a controller for controlling both the dimmer and the shutter by adjusting the exposure time and/or intensity level so that a predetermined quantity of light energy is delivered to the work site.

As it is apparent, the UV light curing system shown in the '729 patent utilizes an internal timer, which is commercially available, to control the shutter actuation. A trip signal is usually a ground connection that is made by use of an external footswitch. To interface with an external processor a relay must be used to complete the trip circuit. In the electromechanical relay, it is advantageous to eliminate oxidation and/or wear of the contacts in order to avoid either partial or total loss of current. Also, a timer must be pre-set independent of the main processing unit. This arrangement is costly due to the additional cost associated with a timer integrated to the curing unit and makes it less flexible to be interfaced with an external system or processor.

It is therefore desirable to provide a UV curing lamp assembly wherein the assembly may be more economically and easily manufactured, and further, allowing the operation of the assembly unit to be externally controlled and its function is fully integrated with other operational components of the complete automated system.

SUMMARY OF THE INVENTION

The present invention provides an electromagnetic energy spot curing system and method of achieving the same. The system includes a curing unit having a radiation source positioned to irradiate a work piece with radiation energy; and a shutter for moving selectively to allow exposure of radiation energy from the source. The system further includes a processor external to the curing unit for providing an external output signal to control the exposure of radiation energy wherein the processor is integrated with the curing unit.

DETAILED DESCRIPTION OF THE INVENTION

The subject invention relates to an electromagnetic energy spot curing system which utilizes a source of radiation found in the electromagnetic spectrum (e.g., ultraviolet (UV); visible light (VIS); infrared). To describe the invention and illustrate its functioning, reference is made herein to the use of a UV lamp. It is to be understood that the UV lamp can be interchanged with other sources of electromagnetic energy. In addition, the electromagnetic energy source may provide electromagnetic energy of varying intensities and/or of varying wavelengths (e.g., various types of radiation).

Figure 1:
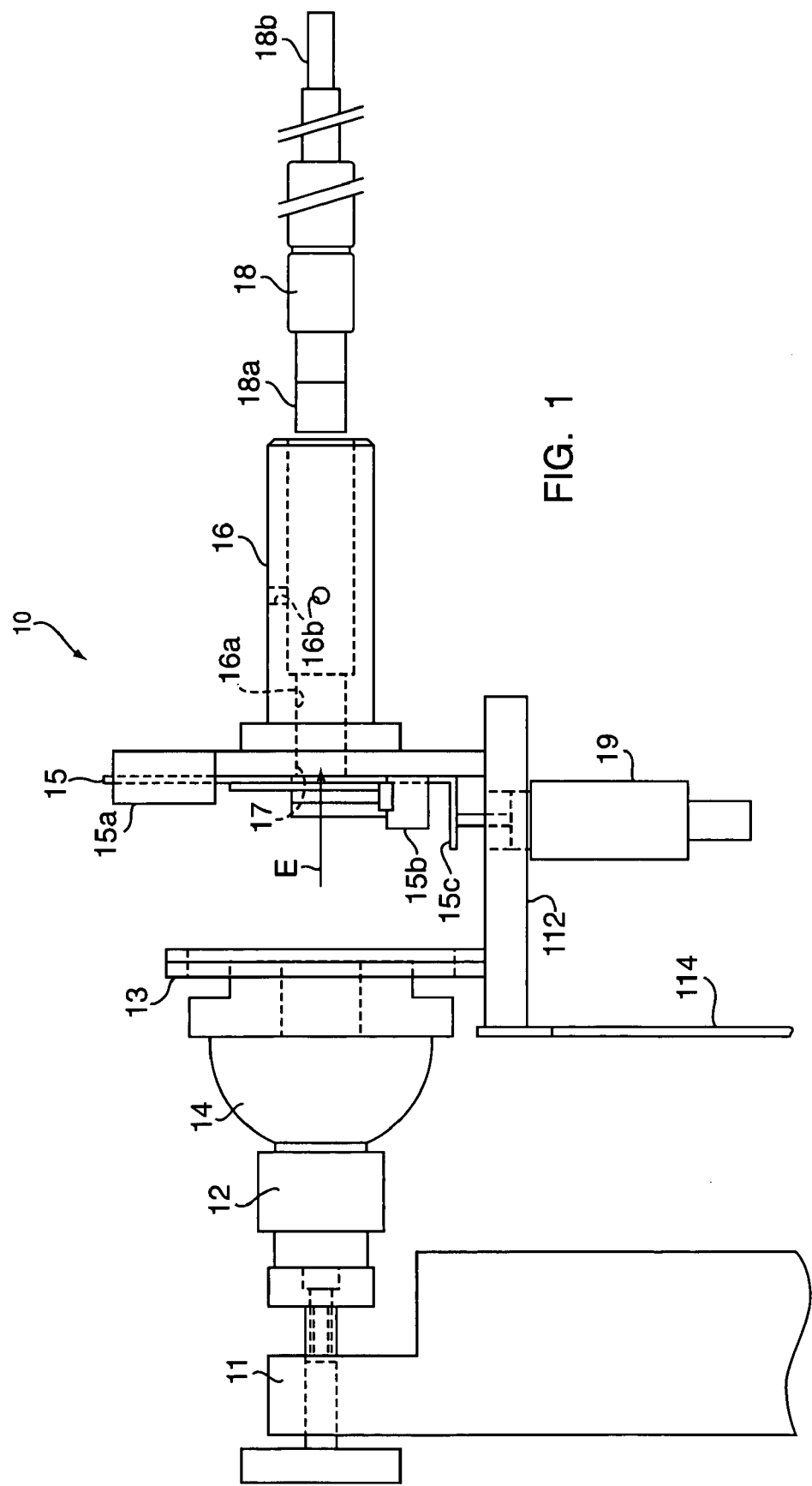
FIG. 1 is a side elevational view of components of the UV/VIS curing system in accordance with the subject invention.
Figure 2:
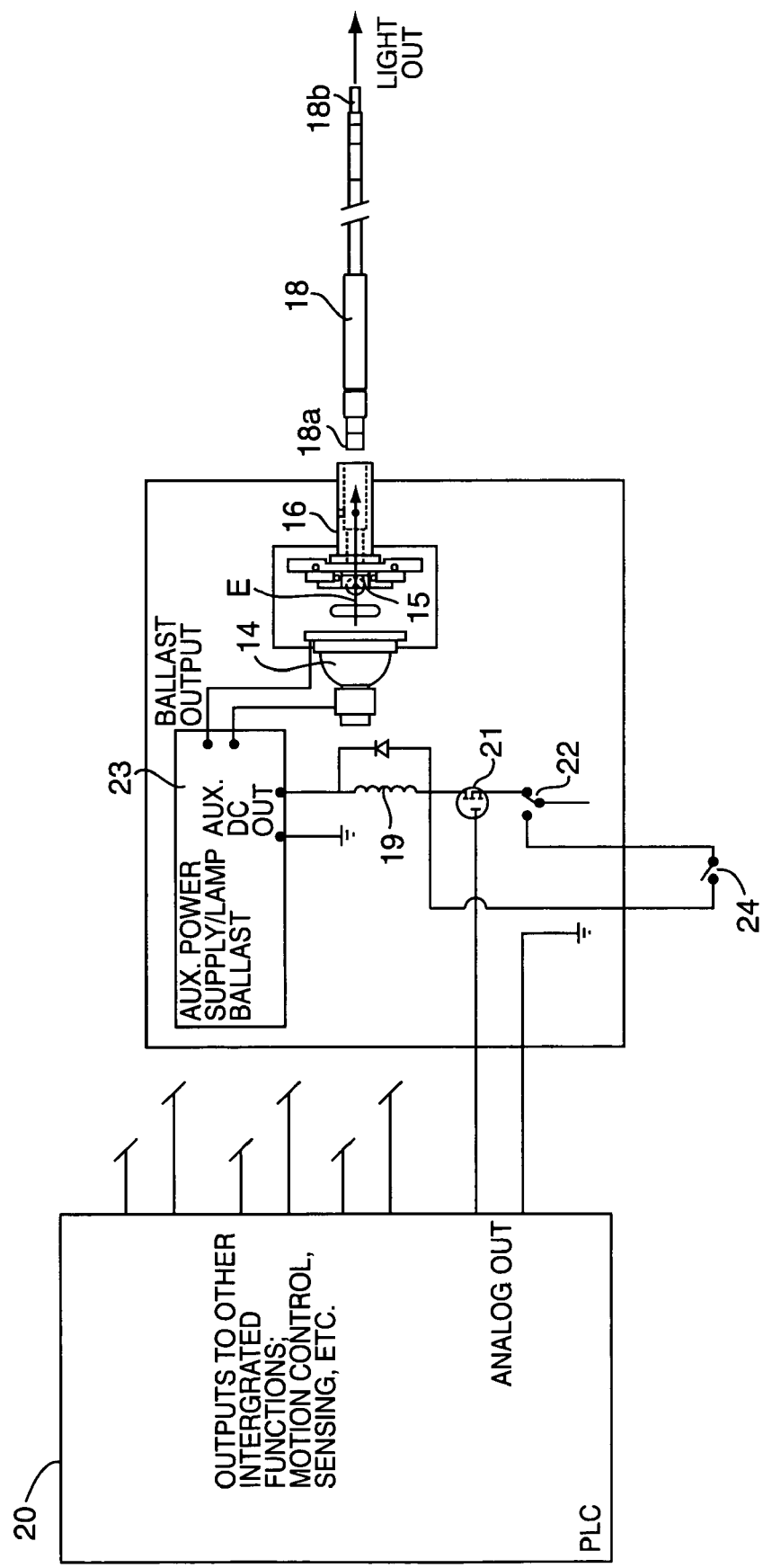
FIG. 2 is a side elevational view of an operating circuit diagram of the UV/VIS curing system of FIG. 1.

With reference to FIGS. 1 and 2, a UV energy spot curing system is generally shown and designated therein with the reference numeral 10.

The system 10 includes a UV lamp 12 mounted between a lamp retainer 11 and a lamp mounting plate 13. The UV lamp 12 preferably is supplied within an elliptic reflector 14 so that the energy emanated from the UV lamp 12 is focused at a precise desired location such as an adhesive on a work-piece surface. A shutter 15 shaped as an inverted "L" is positioned generally parallel to the lamp mounting plate 13 to selectively control UV energy emanating from the lamp 12. The shutter 15 includes shutter guides 15a and 15b placed on top and bottom of the shutter 15 and an opening of generally circular configuration (not shown) located preferably between the guides. The shutter guides 15a and 15b basically place the shutter 15 in place. As will be discussed later, the shutter 15 is moveable to slide up and down within the guides 15a and 15b.

The system 10 further includes a light guide receptacle 16 which is a hollow tube positioned opposite the shutter 15 from the UV lamp 12 with a focused UV energy beam E being directed into an inlet aperture 17 of the light guide receptacle 16. A light guide 18 is positioned to be supported by the light guide receptacle 16. Light guide receptacle 16 is a hollow tube having an opening 16a for supportable receipt of the light guide 18 therein. Light guide receptacle 16 is formed of aluminum, although other materials may be used. The light guide 18 may be secured in the light guide receptacle 16 by screws (not shown) affixed thereto through threaded openings 16b. The light guide 18 may be glass, optical fiber or any other suitable light transmission material known in the art, and is preferably of the liquid-filled type. The light guide 18 includes a light entrance end 18a which plugs into the receptacle 16 and a light output end 18b which may be directed to a work site or target which contains adhesive material to be light cured. The light guide receptacle 16 acts to at least partially collimate the UV beam E, as the beam is emitted from the light guide receptacle 16 into the light guide 18 and exposed to the work site via light output end 18b.

The UV lamp 12 may preferably be a conventional straight mercury arc lamp, metal halide mercury lamp, a xenon-metal halide lamp or any other suitable radiation emitting lamps known in the art. The lamp 12 is controlled by a ballast 23. Ballast 23 is a known electrical device or chip used in fluorescent and HID fixtures for starting and regulating fluorescent and high intensity discharge lamps. Ballast 23 acts as a power regulating source providing sufficient increasing power for the lamp 12 and further controlling the level of power supplied to the lamp 12. To ensure alignment of the UV lamp 12, the shutter 15, the lamp mounting plate 13 and the light guide 16, it is preferred that all these components be fixed to a common base plate 112 to minimize misalignment therebetween. A rear support bracket 114 may be fastened to the base plate 112 to rigidify the structure.

The mechanism for movement of the shutter 15 is described herein. The shutter 15 is generally planar as shown in FIGS. 1 and 2 is connected to one end of a mounting plate (not shown). The mounting plate has a hole through which a light guide receptacle 16 passes through. The shutter 15 is positioned generally planar to the lamp 12 to selectively control UV energy emanating from the system 10. Preferably, the shutter 15 is located to selectively control UV energy entering the inlet aperture 17. The projecting bottom portion 15c of the shutter is suitably connected to a solenoid 19 in the common base plate 112. The opening and closing of the shutter 15 is controlled by a solenoid 19 which may preferably be coupled to the shutter 15. Upon receiving appropriate signals, the solenoid 19 is activated or energized to push the shutter 15 to move up and down the guides 15a and 15b. This movement of the shutter 15 will either allow or prevent the transmission of light through the light guide 16. In other words, when solenoid 19 is activated, it moves the shutter 15 in a first position wherein the circular hole of the shutter 15 coincides or aligns with the light guide 18, thereby allowing the energy/light beam E from the UV lamp 12 to pass through the opening of shutter 15 into the inlet aperture 17 to the light entrance end 18a and emit light via the light output end 18b to the worksite. In a second position the opening of the shutter 15 is not aligned with the light guide 18 which covers the inlet aperture 17 thereby preventing the light beam E from the lamp 12 from reaching the light entrance end 18b. Preferably, the shutter selectively controls UV energy entering the inlet aperture 17. Although not shown, a rotating template may preferably be placed in alignment with a UV lamp 12 to vary UV energy intensity.

The appropriate signals needed to activate the solenoid 19 are received from a PLC 20 or other known processor external to the UV spot curing assembly 10 in accordance with the present invention. As shown in FIG. 2, PLC 20 provides analog voltage signals to a transistor in the curing unit. The preferred transistor type is a metal-oxide-semiconductor-field-effect-transistor (MOSFET) 21. MOSFET is a device commercially available and is used in power electronics applications to amplify electrical signals. The MOSFET typically provides both current and voltage gain yielding an output current into an external load which exceeds the input current and an output voltage across that external load which in turn exceeds the input voltage. In the present invention, the external load is the solenoid 19 of FIGS. 1 and 2. The analog output signal preferably a low voltage signal ranging from 5 V to 25 V of the external PLC 20 provides voltage to gate of MOSFET 21, thereby turning on the MOSFET 21. The MOSFET 21, then, as mentioned earlier, yields an output current, which runs up to the coil of the solenoid 19, thereby activating the solenoid 19 to move the shutter 15, allowing transmission of light through the light guide 16. In this manner, the exposure of the light energy and its exposure time is controlled externally by the processor 20.

Furthermore, in an alternate embodiment, the curing unit can be operated independent from PLC 20. An override switch 22 as shown in FIG. 2 is preferably connected to the MOSFET 21 to have an option to manually open and close the shutter 15 from an external foot switch 24. The switch 22 of FIG. 2 is shown in a position where the MOSFET 21 is prevented from operating, breaking the source of the MOSFET 21 to ground. There will be no current running in MOSFET 21 to activate the solenoid 19. However, when the switch 22 is turned upward it is connecting the MOSFET 21 to the ballast 23. The ballast 23 then supplies the power to turn on the MOSFET 21 which in turn activates the solenoid 19. PLC 20 may or may not be providing the voltage signal to the MOSFET 21. In this position, the voltage signal is being provided by ballast 23 which is part of the curing unit 10. In either manner, the MOSFET 21 will continue to receive the voltage signal to continue the operation of the curing unit 10.

The overall operation of the curing unit 10 as discussed above is controlled from the external processor PLC 20. In other words, the connection of the PLC 20 to the gate of MOSFET 21 turns the MOSFET 21 on which in turn activates the solenoid 19 to control the shutter 15 actuation. This overall operation or process is of the curing unit 10 is completely automated and fully integrated with the operational components of the PLC 20. As a result of this operation, material can be cured with exposure and the dwell periods of the radiation energy being controlled externally.

The devices and the system of the present invention can be used in conjunction with a variety of different photocurable adhesive compositions. For example, UV curable vinyl and (meth)acrylate-containing compositions, which may also be optionally anaerobically curable, may be employed. Such compositions may include urethane-acrylate copolymers and block copolymers such as those disclosed in U.S. Pat. Nos. 3,425,988; 4,295,909; and 4,309,526. Other useful photocurable compositions containing reactive (meth)acrylate components are disclosed in U.S. Pat. Nos. 4,415,604; 4,424,252; and 4,451,523, all to Loctite Corporation.

Photoinitiators which are intended to be active primarily in the ultraviolet (UV) region are incorporated along with the curable component, and which upon exposure to sufficient ultraviolet light initiate photopolymerization of the curable component. Such UV compositions can be used as structural adhesives, potting compounds, gap filling compounds, sealing compounds, conformal coatings as well as other applications known to those skilled in the art.

In addition to the aforementioned adhesive compositions, UV curable silicone compositions are also contemplated as being useful with the present invention. Such compositions contain a curable silicone component and a UV photoinitiator component. Additionally, cyanoacrylate adhesives designed to cure upon exposure to photoirradiation may also be employed.

Examples of commercially available UV curing compositions include Loctite product numbers Adhesive 352, 3321, 3491, 3525 and 3201.

Having described the preferred embodiments herein, it should be further appreciated that various modifications may be made thereto without departing from the contemplated scope of the invention. As such, the preferred embodiments described herein are intended in an illustrative rather than a limiting sense. The true scope of the invention is set forth in the claims appended hereto.

What is claimed is:

1. An electromagnetic energy spot curing system comprising:

a curing unit having a radiation source positioned to irradiate a work piece with radiation energy and having a shutter selectively operable to allow exposure of radiation energy from said source wherein said shutter includes an opening;

a light guide positioned to receive the radiation energy from said source and;

a processor external to the curing unit for providing an externally output signal to control the movement of the shutter, wherein said movement includes a first position such that the opening of the shutter aligns with the light guide and said movement includes a second position such that the opening of the shutter does not align with the light guide.

2. The system of claim 1 wherein said curing unit further comprises a light guide receptacle positioned opposite the shutter.

3. The system of claim 2 wherein said light guide receptacle includes an opening for supportable receipt of the light guide therein.

4. The system of claim 3 wherein said movement of the shutter to the first position allows the radiation energy from the source to pass through said opening of the shutter to irradiate on said work piece.

5. The system of claim 4 wherein said movement of the shutter to the second position, prevents the radiation energy from the source to pass through said opening of the shutter.

6. The system of claim 1 wherein said curing unit further comprises a solenoid connected to bottom of said shutter for controlling movement of the shutter.

7. The system of claim 6 wherein said curing unit further comprises a transistor power circuit connected to the processor via a switch for receiving externally output signal.

8. The system of claim 7 wherein said transistor power circuit is coupled to the solenoid for activating the solenoid upon receipt of said externally output signal from said processor.

9. The system of claim 8 wherein said source is a UV lamp.

10. A method of spot curing a work piece using radiation in the electromagnetic energy comprising:

providing a source of electromagnetic energy using a curing unit, wherein said curing unit includes a shutter having an opening;

emanating radiation from said source for exposure of radiation energy to be received by a light guide; and providing an externally output signal external to the curing unit, thereby causing movement of the shutter to a first position and a second position, wherein said first position includes said opening of the shutter aligning with the light guide and said second position includes said opening of the shutter not aligning with the light guide.

11. The method of claim 10 wherein said movement of the shutter controls the exposure of the radiation energy on said work piece to be cured.

12. The method of claim 11 wherein said movement of the shutter, controls periods of the exposure of the radiation energy on said workpiece to be cured.

13. The method of claim 11 wherein said movement of the shutter to the first position allows the radiation energy to be exposed on said work piece for a period of time.

14. The method of claim 11 wherein said movement of the shutter to the second position prevents the radiation to be exposed to the work piece.

15. The method of claim 10 wherein said externally output signal is provided by a processor.

16. The method of claim 10 wherein said electromagnetic energy source is a UV lamp.

17. The method of claim 10 wherein said work piece includes a curable adhesive.

* * * * *